United States Patent [19]

Granzer et al.

[11] Patent Number: 4,705,792
[45] Date of Patent: Nov. 10, 1987

[54] 4-AMINO-2-(IMIDAZOLIDIN-2-ON-1-YL)-5-(3-TRIFLUOROMETHYL-PHENYL-LAMINOCARBONYL)PYRIMIDINES FOR ANTITHROMBOTIC PROPHYLAXIS AND TREATMENT

[75] Inventors: Ernold Granzer, Kelkheim; Klaus-Dieter Kampe, Bad Soden am Taunus, both of Fed. Rep. of Germany

[73] Assignee: Hoechst Aktiengesellschaft, Frankfurt, Fed. Rep. of Germany

[21] Appl. No.: 878,854

[22] Filed: Jun. 25, 1986

[30] Foreign Application Priority Data

Jun. 27, 1985 [DE] Fed. Rep. of Germany ....... 3522940

[51] Int. Cl.⁴ ................. C07D 239/42; A61K 31/505
[52] U.S. Cl. .................................... 514/275; 544/325
[58] Field of Search ......................... 514/275; 544/325

[56] References Cited

U.S. PATENT DOCUMENTS 4,285,946  8/1981  Kampe et al. ...................... 514/275

Primary Examiner—John M. Ford
Attorney, Agent, or Firm—Finnegan, Henderson, Farabow, Garrett & Dunner

[57] ABSTRACT

4-Amino-2-(imidazolidin-2-on-1-yl)-5-(3-trifluoromethylphenylaminocarbonyl)pyrimidine of the formula I

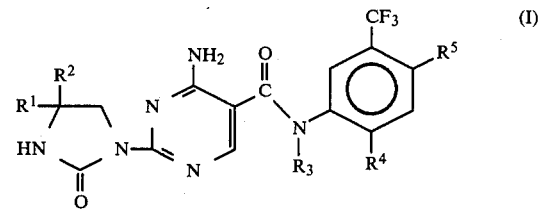

in which $R^1$, $R^2$, $R^3$, $R^4$ and $R^5$ have the indicated meanings, and their physiologically tolerated acid addition salts for the prophylaxis and therapy of thromboses, and the use of these compounds for the preparation of a medicament for the prophylaxis and therapy of thromboses are described.

3 Claims, No Drawings

4-AMINO-2-(IMIDAZOLIDIN-2-ON-1-YL)-5-(3-TRI-FLUOROMETHYL-PHENYLLAMINOCAR-BONYL)PYRIMIDINES FOR ANTITHROMBOTIC PROPHYLAXIS AND TREATMENT

The invention relates to 4-amino-2-(imidazolidin-2-on-1-yl)-5-(3-trifluoromethylphenylaminocarbonyl)-pyrimidines of the formula I

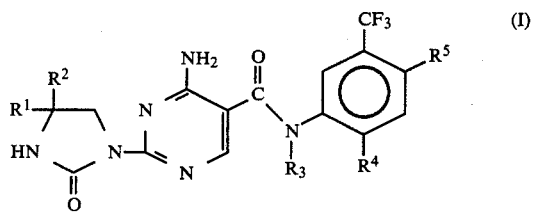

in which
$R^1$ denotes hydrogen, a ($C_1$–$C_3$)-alkyl group or a vinyl group,
$R^2$ denotes a methyl or ethyl group,
$R^3$ denotes hydrogen or a methyl group,
$R^4$ and $R^5$, which are identical or different, denote hydrogen, fluorine or chlorine,
it not being permissible for $R^4$ and $R^5$ both simultaneously to denote fluorine or chlorine, but $R^5$ denoting hydrogen if $R^4$ denotes fluorine or chlorine, and $R^4$ denoting hydrogen if $R^5$ denotes fluorine or chlorine, and to their physiologically tolerated acid addition salts for the prophylaxis and therapy of thromboses.

At present, the following medicaments or groups of medicaments are mainly used to prevent thromboses:

A. Heparin and heparinoid substances which intervene in blood coagulation and which inhibit blood coagulation and thus prevent the development of a thrombus. Their use is restricted since, because of a lack of absorption on oral administration, they can be used only parenterally or in the form of ointments. Hence their preferred area of use is the treatment of superficial vein thromboses with ointments. However, the use to prevent post-operative venous thromboses is greatly restricted owing to their intervention in blood coagulation which thus considerably increases the risk of post-operative hemorrhages.

B. Dicoumarols and other compounds which, owing to competition with vitamin K, likewise intervene in the process of blood coagulation were formerly used for the prophylaxis and after-treatment of myocardial infarct. A prerequisite for their use is regular checks of the inhibition of coagulation, it being expedient to adjust to a 30% normal prothrombin time in order to prevent the possibility that severe hemorrhages likewise occur. However, this group of medicaments can be administered orally.

C. Medicaments of the urokinase or streptokinase type have in recent years been used principally for the treatment of thrombotic causes or complications of myocardial infarct. These can likewise be used only parenterally, and successful use is linked to the administration being as rapid as possible after the myocardial infarct has taken place in order to prevent clot formation by means of plasminogen activation or to dissolve thrombi which are being produced. Apart from systemic, intravenous administration which, however, results in problems of a general tendency to hemorrhage, particular importance attaches to their intracoronary administration using a catheter.

From these notes emerge the prerequisites for successful use of these medicaments:
1. they must be administered soon after a myocardial infarct,
2. they must be administered by the intravenous route or by the intracoronary route using a catheter, and
3. because of the systemic activation of plasminogen there must be expected to be an increased tendency to hemorrhage. In the case of streptokinase its antigenicity is an additional complication which prevents prolonged therapy or repeated therapy because of its immunogenicity in humans.

D. Acetylsalicylic acid and its formulations as platelet aggregation inhibitors have not resulted in an adequate protection from thrombosis in humans on objective examination; none of the studies to date has been able to demonstrate their efficacy by statistical criteria. Questions of dosage which result from the fact that acetylsalicylic acid is an inhibitor of cyclooxygenase and intervenes, before the pathway divides, in the undesired formation of thromboxane (of the platelets) and in the desired formation of prostacyclin (in the vessel walls) are the possible reason why protection from thrombosis has not been demonstrated.

E. There are as yet insufficient findings available on the benefits of specific thromboxane synthetase inhibitors and thromboxane antagonists in humans. Thus antithrombotic therapy using platelet aggregation inhibitors is not free of problems either.

Owing to the intervention of the classic antithrombotics of the heparinoid and dicoumarol types in blood coagulation, there is always a risk when they are used in hypertensive patients that severe and uncontrollable cerebral hemorrhages will be provoked. Hence, the result is a continuing need for antithrombotics which can prevent the formation of thrombi and dissolve thrombi without systemic intervention in blood coagulation, especially since 85% of acute myocardial infarcts are provoked by thrombus formation.

European Pat. No. 0,012,361 (corresponding to U.S. Pat. No. 4,285,946) describes 4-amino-2-(imidazolidin-2-on-1-yl)-5-(3-trifluoromethylphenylaminocarbonyl)-pyrimidines which, because of their anorectic effects, can be used for the treatment of obesity and, because of favorable effects on lipid metabolism, can be used for the treatment of disturbances of lipid metabolism.

It has now been found, surprisingly, that some of the compounds claimed in European Pat. No. B 0,012,361 (corresponding to U.S. Pat. No. 4,285,946) have antithrombotic activity and thus are suitable for the control and prevention of all pathological states based on the formation of thrombi.

Thus the invention relates to 4-amino-2-(imidazolidin-2-on-1-yl)-5-(3-trifluoromethylphenylaminocarbonyl)-pyrimidines of the formula I and to their physiologically tolerated acid addition salts for the prophylaxis and therapy of thromboses.

The invention also relates to medicaments which have antithrombotic activity and which contain compounds of the formula I or their physiologically tolerated salts, and to the use of compounds of the formula I and of their physiologically tolerated salts for the preparation of medicaments for the prophylaxis and therapy of thrombi.

Examples of specific compounds of the general formula I which have antithrombotic activity and which may be mentioned are: 4-amino-2-(4-methyl-4-propylimidazolidin-2-on-1-yl)-5-(3-trifluoromethylphenylaminocarbonyl)pyrimidine; 4-amino-2-(4,4-dimethylimidazolidin-2-on-1-yl)-5-(2-fluoro-5-trifluoromethylphenylaminocarbonyl)pyrimidine; 4-amino-2-(4,4-dimethylimidazolidin-2-on-1-yl)-5-trifluoromethylphenylaminocarbonyl)pyrimidine; 4-amino-2-(4-methyl-4-vinylimidazolidin-2-on-1-yl)-5-(3-trifluoromethylphenylaminocarbonyl)pyrimidine; 4-amino-2-(4,4-dimethylimidazolidin-2-on-1-yl)-5-(N-methyl-N-(3-trifluoromethylphenyl)aminocarbonyl)pyrimidine; 4-amino-2-(4,4-dimethylimidazolidin-2-on-1-yl)-5-(4-chloro-3-trifluoromethylphenylaminocarbonyl)pyrimidine, 4-amino-2-(4-ethyl-4-methylimidazolidin-2-on-1-yl)-5-(3-trifluoromethylphenylaminocarbonyl)pyrimidine; 4-amino-2-(4-ethylimidazolidin-2-on-1-yl)-5-(3-trifluoromethylphenylaminocarbonyl)pyrimidine; 4-amino-2-(4-methyl-4-propylimidazolidin-2-on-1-yl)-5-(2-fluoro-(or 2-chloro)-5-trifluoromethylphenylcarbonyl)pyrimidine; and their physiologically tolerated acid addition salts.

Especially suited for the treatment and prevention of thrombotic states are 4-amino-2-(4,4-dimethylimidazolidin-2-on-1-yl)-5-(3-trifluoromethylphenylaminocarbonyl)pyrimidine (formula I a)

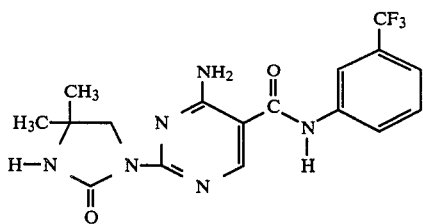

and physiologically acceptable acid addition salts of this compound.

Suitable physiologicaly acceptable salts of the compounds of the formula I according to the invention are those with inorganic and organic acids such as, for example, hydrochloric, hydrobromic or hydriodic, sulfuric, phosphoric, nitric, benzenesulfonic, toluenesulfonic, sulfamic, methylsulfuric, acetic, propionic, oleic, palmitic, stearic, malonic, maleic, succinic, glutaric, malic, tartaric, citric, fumaric, lactic, glycolic, pyruvic, benzoic, toluylic, glutamic, furanecarboxylic, salicylic or mandelic acid. Physiologically tolerated salts with inorganic acids or with strongly or moderately strongly acidic derivatives of such acids are preferred.

The preparation of the compounds of the general formula I which are to be used according to the present invention is described in European Pat. No. 0,012,361 (corresponding to U.S. Pat. No. 4,285,946). It is expediently carried out by the synthetic method described under "b").

For example, it is possible to prepare 4-amino-2-(4,4-dimethylimidazolidin-2-on-1-yl)-5-(3-trifluoromethylphenylaminocarbonyl)pyrimidine (formula I a) by reaction of 1-amidino-4,4-dimethyl-2-imidazolidinone or its acid addition salts with 2-cyano-3-ethoxy-N-(3-trifluoromethylphenyl)acrylamide in accordance with the diagram below.

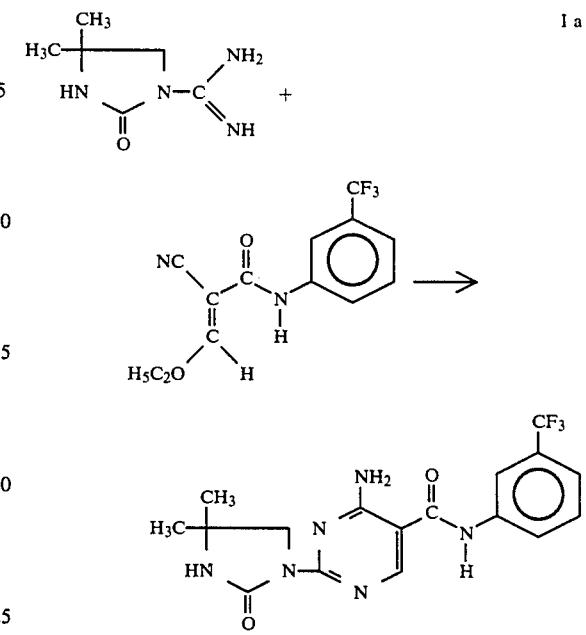

The synthesis of the starting compounds has been described in European Pat. No. 0,012,361.

It has been possible to establish the antithrombotic action of the compounds of the formula I in the following investigations.

In a modified design of the animal model which was used first by Meng and is described in detail in Arzneimittel-Forschung 29, 54 (1979), thrombi are produced by local vessel damage to the carotid artery and jugular vein of rats by refrigeration of the vessel and exertion of pressure on these vessel sites. Compared with a control group, pretreatment of the animals with the compounds of the formula I results either in more animals being kept free of thrombi or the extent (defined by the weight) of the resulting thrombi being markedly reduced; thus, compared with a parallel control group, the mean weight of the thrombi is markedly lower in the group treated with the product than in the control group.

Male rats received by gavage the amount indicated in the table of the compound which was to be tested, and the control group received only the same amount of solvent (polyethylene glycol 400), on 7 consecutive days. The final administration was given 20 hours before the end of the test, i.e. before the operation to produce thrombi using cryoforceps. In the tests identifed by * in the table treatment took place on only 6 consecutive days with the final administration being 1 hour before the end of the test. In test series (A) the animals received a normal diet containing protein, fat, fiber, minerals, trace elements and vitamins (for example Altromin Kontroll-Diät, manufactured by Altromin GmbH), while in test series B) they received ad libitum during the period of the test a special atherogenic diet which contained 5% lard, 1% cholesterol, 0.3% taurocholic acid and 0.1% propylthiouracil in Altromin standard feed. The thrombi were produced by refrigeration of the vessel wall 4 hours before removal of the thrombi from the vessels. For this purpose, the rats were anesthetized with ether for about 2 to 3 minutes. Following a paramedian skin incision and retraction of the subcutaneous tissue, the carotid artery and jugular vein were exposed by dissection over a length of about 2 cm.

Using cryoforceps, which were brought to a temperature of −15° by passing through cold methanol, a force of 200 g was applied to a length of 12 mm of the exposed carotid artery for 2 minutes. A silver clamp was applied distal from the damaged piece of artery and was left in the animal. The wound was then closed with 2 wound clamps. 4 hours after the operation, the animals were successively anesthetized with 50 mg/kg nembutal i.p., there being simultaneous injection of 2500 U/kg heparin i.p. to prevent acute blood coagulation. After 10 minutes, the wound was opened and a piece of artery about 15 mm in size and containing the resulting thrombus was removed. The removed piece of artery was opened with a longitudinal incision, and the adherent thrombus was dissected out, rinsed and washed in sodium chloride solution and then water, dabbed on high-absorbency filter paper for a few seconds and weighed with an electronic microbalance. The jugular vein was treated in essentially the same way to produce venous thrombi, and the inhibition of the formation of venous thrombi was determined. The mean weight of the thrombi in all the animals in an animal group treated with test substance was compared with the mean weight of the thrombi in all the animals in the control group (absent thrombi being included in the calculation with a weight of 0). As can be seen from the table, with the dosage regimen used there was prevention of thrombus formation, preferentially in the arteries, by 4-amino-2-(4,4-dimethylimidazolidin-2-on-1-yl)-5-(3-trifluoromethylphenylaminocarbonyl)pyrimidine (formula I a), there being inhibition of arterial thrombus formation up to a dose of 0.3 mg/kg/day, and marked inhibition of venous thrombus formation was possible only at higher dosage.

TABLE

| | Dose mg/kg/day | Change in the thrombus wet weight in the carotid artery compared with the control group | in the jugular vein |
|---|---|---|---|
| (A) 4-Amino-2-(4,4-dimethyl-imidazolidin-2-on-1-yl)-5-(3-trifluoromethyl-phenylaminocarbonyl)-pyrimidine | 30 | −89% | |
| | 0.3* | −37% | −18% |
| Acetylsalicylic acid | 10 | −21% | |
| (B) 4-Amino-2-(4,4-dimethyl-imidazolidin-2-on-1-yl)-5-(3-trifluoromethyl-phenylaminocarbonyl)-pyrimidine | 30 | −79% | −68% |
| | 10 | −63% | −6% |
| | 3 | −71% | −1% |
| | 1 | −47% | |
| | 0.3* | −18% | |

The use of the compound of the formula I a causes no intervention in coagulation, which was demonstrated by administration of 10 and 30 mg/kg/day to dogs for 5 weeks and examination of the coagulation behavior by the prothrombin time, the thrombin time and the thromboelastogram; in no case were changes indicating an adverse effect on coagulation (i.e. delay in coagulation) found.

Apart from compounds of the formula I, which are used in the form of the free bases and/or in the form of their pharmaceutically acceptable acid addition salts as medicaments, the medicaments according to the present invention can also contain pharmaceutically acceptable additives, such as diluents and/or vehicles. These are to be understood to be physiologically acceptable substances which are mixed with the active compound to convert it into a form suitable for administration.

Examples of suitable solid or liquid pharmaceutical formulations are tablets, coated tablets, powders, capsules, suppositories, syrups, emulsions, suspensions, drops or injectable solutions and products with protracted release of active compound. Examples of vehicles and diluents which are frequently used and which may be mentioned are various sugars or types of starch, cellulose derivatives, magnesium carbonate, gelatin, animal and vegetable oils, polyethylene glycols, water or other suitable solvents, and water-containing buffers which can be made isotonic by addition of glucose or salts. In addition, it is also possible to use, where appropriate, surface-active agents, colorants and flavorings, stabilizers, and preservatives as further additives in the medicament formulation according to the invention.

The products can be administered orally, rectally or parenterally.

The products can preferably be produced in dosage units. Particular examples of suitable dosage units are tablets, capsules, suppositories and ampuls. Each dosage unit, in particular for oral administration, can contain up to 1000 mg, but preferably 15 to 200 mg, of the active constituent. However, dosage units greater or less than this can be used and have, where appropriate, to be divided or multiplied before administration. Where appropriate, the dosage units for oral administration can be microencapsulated for release to be delayed or extended over a longer period, such as, for example, by coating or embedding of particulate material in suitable polymers, waxes or the like.

Parenteral administration can be effected by use of liquid dosage forms, such as sterile solutions and suspensions which are meant for intramuscular or subcutaneous injection. Dosage forms of these types are prepared by dissolution or suspension of an appropriate amount of active compound in a suitable physiologically acceptable diluent such as, for example, an aqueous or oily medium, and sterilization of the solution or the suspension, where appropriate with additional use of suitable stabilizers, emulsifiers and/or preservatives.

The oral administration form is preferred and represents a considerable facilitation of the treatment of thrombosis.

The pharmaceutical products are prepared by generally customary methods.

Example 1: Tablets

Tablets which are suitable for oral administration and contain the constituents mentioned below are prepared in a manner known per se by granulation of active compounds and auxiliaries and then compressing them to form tablets. These tablets are suitable for antithrombotic treatment in a dose of one tablet 2-4 times a day.

| Constituents (per tablet) | Weight (mg) |
|---|---|
| 4-Amino-2-(4,4-dimethylimidazolidin-2-on-1-yl)-5-(3-trifluoromethylphenyl-aminocarbonyl)pyrimidine | 50 mg |
| Lactose | 100 mg |
| Corn starch | 30 mg |
| Talc | 3 mg |
| Colloidal silica | 3 mg |
| Magnesium stearate | 2 mg |

Example 2: Capsules

Capsules which are suitable for oral administration contain the constituents mentioned below and can be prepared in a manner known per se by mixing the active compounds and auxiliaries and dispensing them into gelatin capsules. These capsules are used for antithrombotic treatment in a dose of one capsule 2-4 times a day.

| Constituents (per capsule) | Weight (mg) |
| --- | --- |
| 4-Amino-2-(4,4-dimethylimidazolidin-2-on-1-yl)-5-(3-trifluoromethylphenyl-aminocarbonyl)pyrimidine | 50 mg |
| Lactose | 100 mg |
| Corn starch | 30 mg |
| Talc | 3 mg |
| Colloidal silica | 3 mg |
| Magnesium stearate | 2 mg |

We claim:

1. A method for the treatment of a warm-blooded mammal for the prophylaxis and therapy of thromboses which comprises administering to said mammal a pharmaceutically effective amount for said treatment of a 4-amino-2-(imidazolidin-2-on-1-yl)-5-(3-trifluoromethylphenylaminocarbonyl)pyrimidine of the formula I

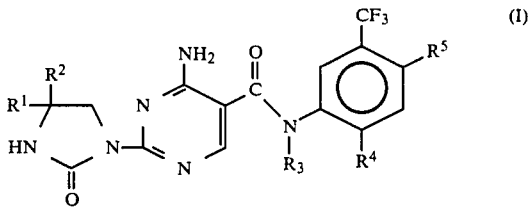

in which $R^1$ is hydrogen, a $(C_1-C_3)$-alkyl group or a vinyl group, $R^2$ is a methyl or ethyl group, $R^3$ is hydrogen or a methyl group, and $R^4$ and $R^5$, which are identical or different, are hydrogen, fluorine or chlorine, with the proviso that $R^4$ and $R^5$ are not both simultaneously fluorine or chlorine, that $R^5$ is hydrogen if $R^4$ is fluorine or chlorine, and that $R^4$ is hydrogen if $R^5$ is fluorine or chlorine, or a physiologicaly tolerated acid addition salt thereof.

2. The method as claimed in claim 1 wherein said compound of formula I or said salt thereof is administered orally to said mammal.

3. The method as claimed in claim 1 wherein said compound of formula I or said salt thereof is administered in the form of a pharmaceutical composition containing said compound or said salt and a pharmaceutically acceptable carrier.

* * * * *